US008656916B2

(12) United States Patent
Stukanov

(10) Patent No.: US 8,656,916 B2
(45) Date of Patent: Feb. 25, 2014

(54) INTRAVAGINAL DEVICE WITH WIRELESS SENSORS ON A CONTRACEPTIVE BARRIER

(75) Inventor: Igor Igorevich Stukanov, Toronto (CA)

(73) Assignee: Igor Stukanov, Toronto, ON (CA)

( * ) Notice: Subject to any disclaimer, the term of this patent is extended or adjusted under 35 U.S.C. 154(b) by 522 days.

(21) Appl. No.: 12/661,098

(22) Filed: Mar. 11, 2010

(65) Prior Publication Data

US 2010/0331720 A1 Dec. 30, 2010

Related U.S. Application Data

(60) Provisional application No. 61/269,350, filed on Jun. 24, 2009.

(51) Int. Cl.
A61F 6/00 (2006.01)
A61F 6/20 (2006.01)
A61B 5/00 (2006.01)
A61B 5/01 (2006.01)

(52) U.S. Cl.
USPC ........... 128/830; 128/832; 128/833; 128/839; 128/841; 600/301; 600/549; 600/587

(58) Field of Classification Search
USPC .................. 600/551, 301, 549, 587; 128/844, 128/830–841; 12/551
See application file for complete search history.

(56) References Cited

U.S. PATENT DOCUMENTS 4,027,670 A * 6/1977 Bronner .................... 604/204
4,616,640 A * 10/1986 Kaali et al. .................... 128/833
4,770,167 A * 9/1988 Kaali et al. .................... 128/832
4,827,946 A * 5/1989 Kaali et al. .................... 128/830
4,922,928 A * 5/1990 Burnhill ..................... 128/832
4,932,421 A * 6/1990 Kaali et al. .................... 128/831
4,971,036 A * 11/1990 Collins .......................... 600/202
5,167,237 A * 12/1992 Rabin et al. .................. 600/561
5,209,238 A * 5/1993 Sundhar ........................ 600/551
5,240,010 A * 8/1993 Weinmann .................... 600/547
5,333,621 A * 8/1994 Denzer .......................... 128/844
5,628,771 A * 5/1997 Mizukawa et al. ........... 607/102
5,928,195 A * 7/1999 Malamud et al. ............. 604/141
6,009,350 A * 12/1999 Renken .......................... 607/32
6,080,118 A * 6/2000 Blythe .......................... 600/591
6,095,969 A * 8/2000 Karram et al. .................. 600/31
6,169,914 B1 * 1/2001 Hovland et al. .............. 600/340
6,234,974 B1 * 5/2001 Catt et al. ..................... 600/551
6,328,687 B1 * 12/2001 Karram et al. .................. 600/31
6,741,895 B1 * 5/2004 Gafni et al. ................... 607/138
6,847,844 B2 * 1/2005 Sun et al. ...................... 607/32
6,896,653 B1 * 5/2005 Vail et al. ...................... 600/135
7,101,343 B2 * 9/2006 Delalic et al. ................. 600/587
7,527,589 B2 * 5/2009 Squicciarini .................... 600/39
7,577,476 B2 * 8/2009 Hochman et al. ............. 600/546
7,957,794 B2 * 6/2011 Hochman et al. ............. 600/546
7,998,060 B2 * 8/2011 Ferren et al. .................. 600/114

(Continued)

FOREIGN PATENT DOCUMENTS

GB         2206799 A  *  1/1989  ............. A61F 5/46
WO   WO 02087446 A1 *  11/2002  ............ A61B 10/00
WO   WO 2010001719 A1 *  2/2010  ............. A61B 5/00

Primary Examiner — Sean Dougherty

(57) ABSTRACT

A convenient and highly accurate intravaginal device with wireless sensors for monitoring fertility and sexual health of humans and animals is proposed. Sensors in the intravaginal device measure fertility and sexual health and via wireless transmitter send this information to a terminal on which the information is processed and displayed in convenient form.

5 Claims, 2 Drawing Sheets

(56) References Cited

U.S. PATENT DOCUMENTS

| | | | |
|---|---|---|---|
| 8,070,687 B2* | 12/2011 | Cinti | 600/551 |
| 8,496,597 B2* | 7/2013 | James et al. | 600/551 |
| 2004/0068162 A1* | 4/2004 | Kirsner | 600/300 |
| 2004/0181167 A1* | 9/2004 | Carney et al. | 600/551 |
| 2005/0096562 A1* | 5/2005 | Delalic et al. | 600/561 |
| 2005/0215858 A1* | 9/2005 | Vail | 600/135 |
| 2006/0084848 A1* | 4/2006 | Mitchnick | 600/301 |
| 2008/0139875 A1* | 6/2008 | Tracey et al. | 600/29 |
| 2008/0245371 A1* | 10/2008 | Gruber | 128/831 |
| 2009/0107512 A1* | 4/2009 | Hyde et al. | 128/844 |
| 2009/0112055 A1* | 4/2009 | Hyde et al. | 600/38 |
| 2009/0131959 A1* | 5/2009 | Rolland | 606/158 |
| 2009/0143646 A1* | 6/2009 | Vail, III | 600/135 |
| 2009/0171138 A1* | 7/2009 | Eli | 600/33 |
| 2009/0171144 A1* | 7/2009 | Squicciarini | 600/38 |
| 2010/0016668 A1* | 1/2010 | Gal | 600/135 |
| 2010/0033188 A1* | 2/2010 | Rieth | 324/438 |
| 2010/0331720 A1* | 12/2010 | Stukanov | 600/551 |
| 2011/0106465 A1* | 5/2011 | Moons | 702/50 |
| 2011/0190579 A1* | 8/2011 | Ziarno et al. | 600/109 |
| 2012/0040655 A1* | 2/2012 | Larkin | 455/418 |
| 2013/0054150 A1* | 2/2013 | Sacks et al. | 702/19 |

* cited by examiner

INTRAVAGINAL DEVICE WITH WIRELESS SENSORS ON A CONTRACEPTIVE BARRIER

CROSS-REFERENCE TO RELATED APPLICATIONS

This application claims priority status of the provisional patent application 61/269,350 filed on Jun. 24, 2009

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention relates to devices for monitoring fertility and sexual health of human and animals.

2. Background Information

Cost of fertility and unwanted pregnancy related problems exceed one trillion of dollars today and continue to rise. Therefore, there is a need for cheap, safe, convenient and accurate methods to monitor fertility and sexual health.

Fertility kits available today are safe and cheap, but they are not convenient because they require taking samples of fluids from a human body every time to measure a fertility level; also they are not very accurate, because they rely not on direct indicators of fertility, but on non-direct indicators, which correlate with direct indicators. The degree of correlation depends on a set of other variables such as environmental impact, stress, diet, emotional condition, etc., which make the measurement of fertility less accurate.

Fertility monitors are more convenient, but they also not accurate for the same reasons as the fertility kits.

The purpose of the current invention is to suggest a device which allow to monitor fertility and sexual health in safe, cheap, convenient way with high accuracy.

BRIEF SUMMARY OF THE INVENTION

An intravaginal device which allow to monitor fertility and sexual health in safe, cheap, convenient way with high accuracy is proposed. The device consists of a contraceptive barrier such as cervical cap or diaphragm with wireless sensors of fertility indicators, a control unit with wireless transmitter and receiver, and a terminal for receiving, processing and displaying information about fertility and sexual health and controlling the device.

DETAILED DESCRIPTION OF THE INVENTION

The present invention is directed to device, which allow to monitor fertility and sexual health in safe, cheap, convenient way with high accuracy.

Figure 1:
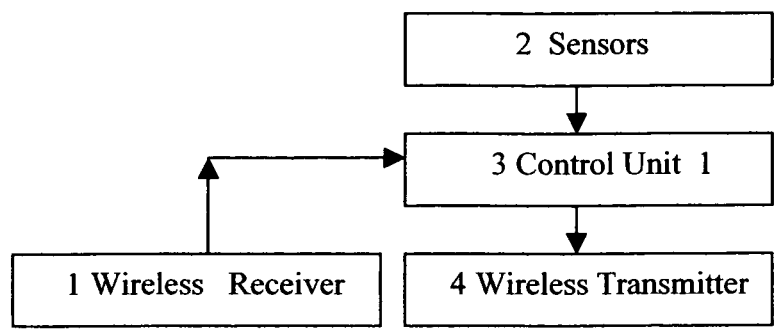
FIG. 1. A structural scheme of the intravaginal device with wireless sensors

FIG. 1 shows simplified scheme of the device, which include a contraceptive barrier such as cervical cap or diaphragm with wireless sensors of fertility indicators, a control unit with wireless transmitter and receiver.

Sensors on the internal side of the contraceptive barrier monitor female fertility and sexual health by measuring direct and indirect fertility indicators such as ultrasonic or infrared images of follicle collapse with egg release, vaginal temperature, physical and chemical properties of vaginal fluids, concentration of hormones and enzymes, folliculogenesis and other ovarian functions. Also these sensors monitor concentration of antibodies and harmful microorganisms for evaluation of sexual health of the female. Sensors on the external side of the contraceptive barrier monitor fertility parameters of the male's sperm (motility, count, morphology) and concentration of antibodies and harmful microorganisms for evaluation of sexual health of the male.

The information from the sensors is compressed by the control unit and is sent to the terminal via wireless transmitter.

The control unit is responsible for turning on/off and control of the sensors, receiver and transmitter. For example, the control unit may be programmed via the terminal to turn on every morning at 8:00 AM, measure the fertility indicators, compress this information, send it to the terminal and turn off the device till the next morning. With modern technology such cycle can be accomplished in a fraction of a second, therefore the total exposure of female vaginal system to electromagnetic radiation can be less than a second per year. As such technology are becoming better and better this time may be reduced in the future, which will make this device very safe with regards to exposure to electromagnetic radiation.

Figure 2:
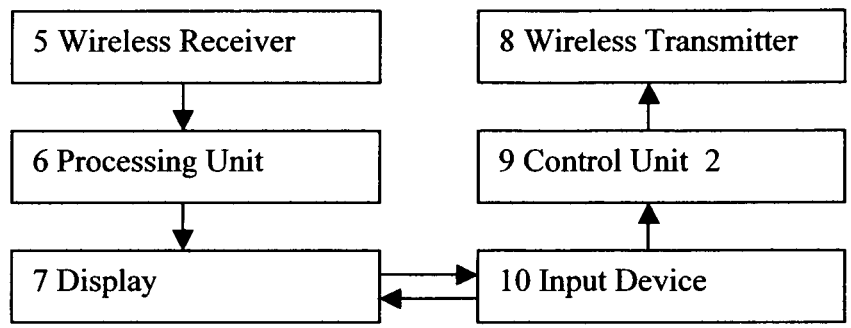
FIG. 2. A structural scheme of a terminal

FIG. 2 shows simplified scheme of the terminal. The terminal receives information from the device via the wireless receiver, processes it by the processing unit according to a proprietary or known algorithm and displays it on the terminal's screen. The terminal may be any portable wireless device such as pc, netbook, notebook, smart phone, mobile phone, ipod, ipad, PDA, etc. The terminal also sends information and instructions to the control unit of the device via the wireless transmitter.

Figure 3:
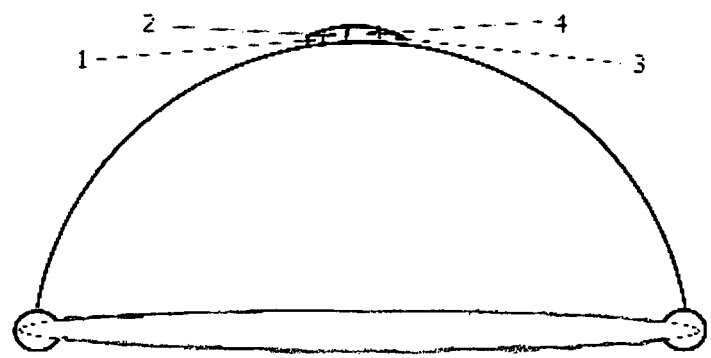
FIG. 3. A design with placement of the device's modules on the internal side of a contraceptive diaphragm.

On FIG. 3 it is shown a design of the device where sensors (2), control unit (3), wireless receiver (1) and transmitter (4) are placed on the internal side of a contraceptive diaphragm or cap.

Figure 4:
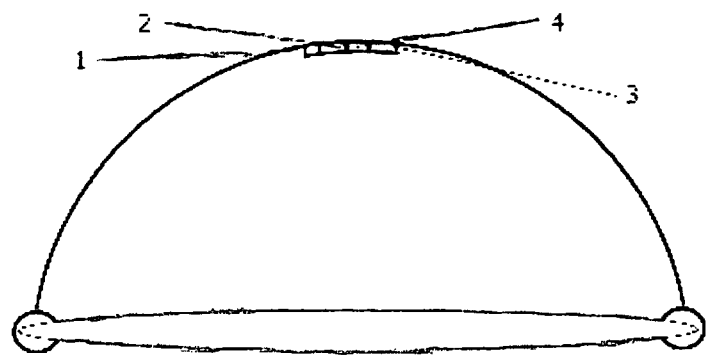
FIG. 4. A design with placement of the device's modules on the external side of a contraceptive diaphragm.

On FIG. 4 it is shown a design of the device where sensors (2), control unit (3), wireless receiver (1) and transmitter (4) are placed on the external side of a contraceptive diaphragm or cap.

Figure 5:
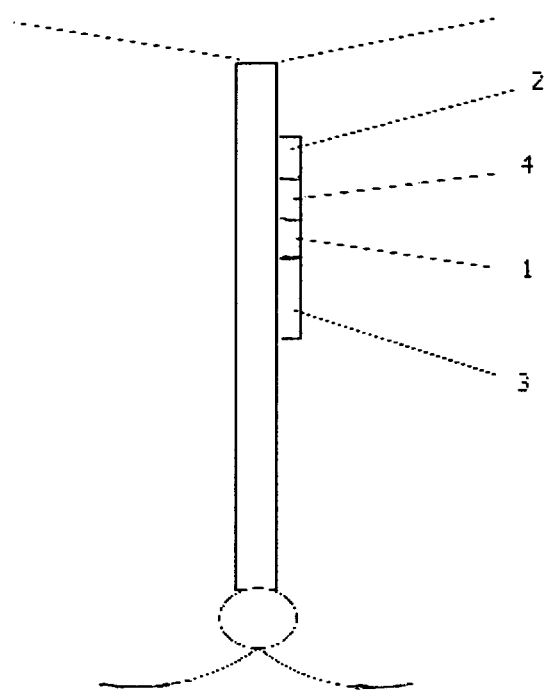
FIG. 5. A design with placement of the device's modules on a contraceptive spiral/IUD.

On FIG. 5 it is shown a design of the device where sensors (1), control unit (3), wireless receiver (1) and transmitter (4) are placed on a contraceptive spiral/IUD.

The invention claimed is:

1. A device for wireless monitoring of fertility and sexual health of humans and animals comprising:
   a female contraceptive barrier;
   one or more sensors for measuring female fertility and sexual health, placed on an internal side of said barrier;
   one or more sensors for measuring male fertility and sexual health, placed on an external side of said barrier;

a control unit, which turns on and off said device, compresses information from said sensors and sends the information to a terminal for processing the information and displaying results;

a wireless transmitter, where the information sent to the terminal for processing the information and displaying results is performed by the wireless transmitter;

a wireless receiver, where instructions to said control unit are received from the terminal by the wireless receiver.

2. The device as in claim 1, where one of said sensors is capable of taking ultrasonic images of follicle collapse with egg release.

3. The device as in claim 1, where one of said sensors is capable of taking infrared images of follicle collapse with egg release.

4. The device as in claim 1, where one of said sensors is capable of measuring vaginal temperature.

5. The device as in claim 1, where one of said sensors is capable of measuring concentration of enzymes.

\* \* \* \* \*